(12) United States Patent
Rabello et al.

(10) Patent No.: US 6,818,402 B2
(45) Date of Patent: Nov. 16, 2004

(54) METHOD AND KIT FOR THE DETECTION OF SCHISTOSOMIASIS THROUGH THE POLYMERASE CHAIN REACTION

(75) Inventors: Ana Lúcia Teles Rabello, Minas Gerais (BR); Emmanuel Dias Neto, São Paulo (BR); Luís André Pontes, Minas Gerais (BR)

(73) Assignee: Fundacao Oswaldo Cruz - Fiocruz, Rio de Janeiro (BR)

( * ) Notice: Subject to any disclaimer, the term of this patent is extended or adjusted under 35 U.S.C. 154(b) by 0 days.

(21) Appl. No.: 09/980,277
(22) PCT Filed: Apr. 4, 2001
(86) PCT No.: PCT/BR01/00035
§ 371 (c)(1),
(2), (4) Date: Mar. 29, 2002
(87) PCT Pub. No.: WO01/75148
PCT Pub. Date: Oct. 11, 2001

(65) Prior Publication Data
US 2003/0096244 A1 May 22, 2003

(30) Foreign Application Priority Data
Apr. 4, 2000 (BR) .............................................. 0001536

(51) Int. Cl.[7] .......................... C12Q 1/68; C12P 19/34; C07H 21/04
(52) U.S. Cl. .......................... 435/6; 435/91.2; 435/810; 536/23.1; 536/23.7; 536/24.32; 536/24.33; 204/461
(58) Field of Search ........................... 435/6, 91.2, 810; 536/23.1, 23.7, 24.32, 24.33; 204/461

(56) References Cited

PUBLICATIONS

Hamburger, J. et al. Polymerase chain reaction assay for detecting snails infected with bilharzia parasites (*Schistosoma mansoni*) from very early prepatency.*

Jannotti–Passos, L.K. et al. PCR amplification of the mitochondrial DNA minisatellite region to detect *Schistosoma mansoni* infection in *Biomphalaria glabrata* snails. Journal of Parasitology 83(3):395–399 (1997).*

Ahern, H. Biochemical, reagent kits offer scientists good return on investment. The Scientist 9(15):20 (Jul. 1995).*

MacCallum, L.J. "Chapter 11: Detection of PCR Amplified Products," PCR Essential Data, C.R. Newton, ed., John Wiley & Sons, Chichester, 1995, pp. 99–103.*

Hamburger, J., Am J. Trop Med Hyg (1998), 59(3), 468–473.

Hamburger, J., Mol. Biochem. Parasitol (1991), 44(1), 73–80.

* cited by examiner

Primary Examiner—Diana B. Johannsen
(74) Attorney, Agent, or Firm—Nixon & Vanderhye P.C.

(57) ABSTRACT

The present invention provides a method of detection of *Schistosoma* sp. in biological samples through PCR, as well as a method for the diagnosis of Schistosomiasis through the amplification by PCR of the DNA sequence of *Schistosoma* sp., followed by the separation of the products of the amplification by electrophoresis and the detection by appropriate technique. Moreover, the present invention provides a kit for the diagnosis to be used in the detection of Schistomsomiasis.

5 Claims, 7 Drawing Sheets

Figure 2:
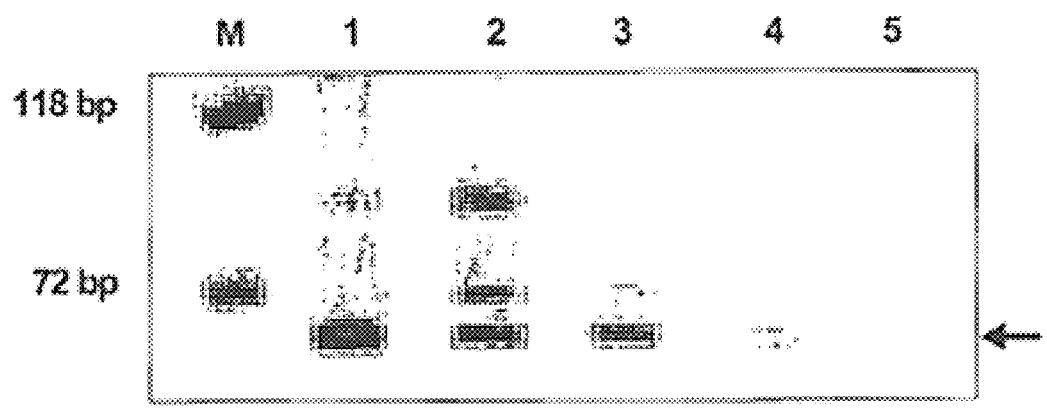

```
GATCTGAATC  CGACCAACCG  TTCTATGAAA  ATCGTTGTAT
CTAGACTTAG  GCTGGTTGGC  AAGATACTTT  TAGCAACATA

CTCCGAAACC  ACTGGACGGA  TTTTTATGAT  GTTTGTTTTA
GAGGCTTTGG  TGACCTGCCT  AAAAATACTA  CAAACAAAAT

GATTATTTGC  GAGAGCGTGG  GCGTTAATAT  AAAACAAGAA
CTAATAAACG  CTCTCGCACC  CGCAATTATA  TTTTGTTCTT
```

FIGURE 1

SEQUENCE LISTING

<160> NUMBER OF SEQ ID NOS: 3

<210> SEQ ID NO 1
<211> LENGTH: 120
<212> TYPE: DNA
<213> ORGANISM: S. mansoni

<400> SEQUENCE: 1

```
gatctgaatc cgaccaaccg ttctatgaaa atcgttgtat ctccgaaacc actggacgga      60
tttttatgat gtttgtttta gattatttgc gagagcgtgg gcgttaatat aaaacaagaa     120
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer
      based on repetitive seq of SEQ ID NO:1

<400> SEQUENCE: 2

```
gatctgaatc cgaccaaccg                                                  20
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer
      based on SEQ ID NO:1

<400> SEQUENCE: 3

```
atattaacgc ccacgctctc                                                  20
```

METHOD AND KIT FOR THE DETECTION OF SCHISTOSOMIASIS THROUGH THE POLYMERASE CHAIN REACTION

This application is the U.S. national phase of international application PCT/BR01/00035 filed Apr. 4, 2001 which designated the U.S.

The present invention relates to a method and kit for the diagnosis of *Schistosomiasis* in human sample matter by Polymerase Chain Reaction (PCR). The method is based on the detection of the parasite DNA and is especially useful in cases of low infection intensity, for which parasitological stool tests (Kato-Katz) demonstrate little sensitivity.

BACKGROUND OF THE INVENTION

Schistosomiasis is a disease caused through infection by parasites of genus *Schistosoma*, with *Schistosoma mansoni*, *Schistosoma japonicum* and *Schistosoma haematobiom* being the principal infectant species. The disease has been recorded for 4000 years and still constitutes an important problem for public health, affecting more than 200 million people in undeveloped countries. The species *S. mansoni* is endemic in 54 countries and territories of South America, the Caribbean, Africa and the eastern Mediterranean region.

These helminths, digenetic trematodes, infect man by penetration of the skin by the cercariae (larval stage), that are eliminated in the water by different species of molluscs, their intermediate hosts. After migrating through the skin, the larvae of *S. mansoni* traverse the lungs and attain the hepatic portal system, then subsisting in the veins and plexus of the gastrointestinal tract, where they become adult and mate, following which the female then deposits approximately 300 eggs per day in the venous vessels.

The immunoreaction of the host to the parasite eggs which will lodge in the tissues is the principal responsable for the spread of the disease. In some cases, it develops into the acute clinical form with intense toxemic manifestations and, in the majority of victims, a debilitating chronic disease, with possibilities of serious and frequently fatal complications.

Amongst the measures to control the infection, the treatment of the infected, the control of the molluscs, the improvement of living conditions and the identification followed by the early treatment of populations at risk have proven to be the most sustainable, but are by no means completely satisfactory. After the seventies, with the advent of drugs usable on a major scale, the specific therapeutic began to play a crucial role in all programs to control the disease.

The method of diagnosis constitutes a primordial instrument for the programs to control the endemic. It is highly desirable to develop techniques that are more efficient than those presently available.

The diagnosis of the infection can be done through confirmation by microscopy of the presence of parasite eggs in the faeces or urine, depending on the species. The Kato-Katz method (KATZ, N., A. Chaves, J. Pellegrino, 1972, A simple device for quantitative stool thick smear technique in *Schistosomiasis mansoni*. Rev. Inst. Med. Trop. São Paulo. 14: 337–340) is the technique that offers the best conditions of efficiency, cost and operation; (WHO, 1994, The Control of schistosomiasis. Technical Report Series, 830, Geneva, 86 pp.). However, when the quantity of eggs in the faeces is small, such as in conditions of low prevalence and low infection intensity and also when is necessary to monitor the treatment, the sensitivity of the test on a single faecal sample is diminished making a greater number of faecal samples examinations necessary. Even so, some victims may not be diagnosed, and consequently, not receive treatment.

The serological diagnosis constitutes an alternative to the parasitological test, being, after the latter, the second most widely employed. By this method, antibodies produced by infection with *S. mansoni* are detected by techniques such as the reaction of indirect immunofluorescence and ELISA (Enzyme Linked ImmunoSorbent Assay). However, this technique has the disadvantage of not distinguishing between active infection and past infection. Thus, the low specificity of antibodies against *S. mansoni* in the absence of active infection is explained by crossed reactivity with other parasites (Corrêa-Oliveira R, Dusse L M S, Viana I R C, Colley D G, Carvalho O S, Gazzinelli G 1988. Human antibody response against schistosomal antigens. Am J Trop Med Hyg 38: 348–355) by the presence of unisexual infections, by contact with other cercariae, by the transfer of maternal antibodies and by the persistance of antibodies after a successful previous treatment.

Another alternative for the diagnosis of *Schistosoma mansoni* consists in detecting antigenic substances released by the parasite, allowing to differentiate between past and active infection and eliminating the problem of the unspecificity of the antibody diagnostic. However, the search for circulating antigens presents other disadvantages, such as low sensitivity to light infections, the high cost, difficulty of operation and a dependency on the production of monoclonal antibodies (D E Jonge,N., A. L. T. Rabello, F. W. Krijger, P. G. Kremsner, R. S. Rocha, N. Katz e A. M. Deelder.1991. Levels of Schistosome circulating anodic and cathodic antigens in serum of Schistosomiasis patients from Brazil. Trans. R. Soc. Trop. Med. Hyg.85:756–759).

With the emergence of Polymerase Chain Reaction (PCR), it has become possible to amplify the DNA of pathogenic organisms enabling that, from minute initial quantities, sufficiently large quantities be obtained to the point of permitting their detection. Thus, PCR has come to be used as an efficient method of diagnosis for the most diverse infections.

Document EP 550 883 describes an experiment using PCR to detect, in faecal matter, the presence of the DNA of protozoan *G. lamblia*. The procedure was carried out using, as target, the sequence of the gene RNA 18S of *G. lamblia*. Furthermore the applicant designed oligonucleotide primers sufficiently complementary to a region of the target sequence of the ribosomic RNA 18S of *G. lamblia*.

Document WO 94/04681 is related to the development of specific oligonucleotides to be used as primers of the PCR for the detection of the DNA sequence encoding the protein of the wall of *Cryptosporidium* sp., and thus as a kit for the diagnostic of parasites of this genera. Apart from the above mentioned examples, it is possible to cite the document WO 93/03167, which is an application of a process for the isolation, storage and cleavage of DNA capable of furnishing it in an adequate form for amplification through a specific sequencial process, such as PCR. The process is particularly employed for the detection of parasitic diseases caused by micro-organisms having concatenated closed circular kinetoplast DNA such as *T. cruzi*, *Leishmania* sp., *P. falciparum*, *P. vivax* and *P. malariae*.

In the study of the *Schistosoma* sp. PCR has been used for determining the sex of the cercariae (Gasser, R. B., G. Morahan e G. F. Mitchell. 1991. Sexing single larval stages of *Schistosoma mansoni* by polimerase chain reaction. Mol.

Bioch. Parasitol. 47:255–258.) in the cloning and sequencing of specific genes (Francis, P. e Q. Bickl.1992. Cloning of a 21.7 kDa vaccine-dominant antigen gene of *Schistosoma mansoni* reveals an Elf Hand-like motif. Mol. Bioch. Parasitol. 50:215–224.; Kiang, D., A. M. Karim, P. T. LoVerde.1996. Cloning the gene encoding *Schistosoma mansoni* p50, an immunophilin. Gene. 170:137–140.), in order to ascertain the populational genetic variability of strains of *Schistosoma* sp. (Dias Neto, E., C. P. Souza, D. Rollinson, N. Katz, and A. J. G. Simpson. 1993. The random amplification of polymorphic DNA allows the identification of strains and species of Schistosomes. Molecular and Biochemical Parasitology 57 (1): 83–88.; Simpson,A. J., E. Dias Neto, T. H. Vidigal, H. B. Pena, O. S. Carvalho e S. D. Pena.1995. DNA polymorphism of schistosomes and their snail hosts. Mem. Inst. Oswaldo Cruz.90(2):211–213.) and in the development and application of techniques for the generation of Expressed Sequence Tags (or EST's) (Dias Neto, E.; Harrop, R., Correia-Oliveira, R., Pena,S. D. J., Wilson,R. A. e Simpson,A. J. G.1996. The schistosome genome project: RNA arbitrarily primed PCR allows the accelerated generation of expressed sequence tags. Mem. Ist. Oswaldo Cruz. 91(5):655–657; Dias Neto, E., Harrop, R., Correa-Oliveira, R., Wilson, R. A., Pena, S. D. J. e Simpson, A. J. G. 1997. Minilibraries constructed from cDNA generated by arbitrarily primed RT-PCR: an alternative to normalized libraries for the efficient generation of ESTs from nanogram quantities of mRNA. Gene 186: 135–142). Recently, Hamburger et al. (Hamburger, J., X. Yu-Xin, R. M. Ramzy, J. Jourdane e A. Ruppel. 1998. Development and evaluation of a Polymerase Chain Reaction for monitoring *Schistosoma mansoni* infestation of water. Am. J. Trop. Med. Hyg. 59(3):468–473) developed a PCR-based test to monitor *S. mansoni* infestation of natural water.

The primers described in the present invention were designed based on the *S. mansoni* sequence originally described by Hamburger et al. shown in FIG. 1, (Hamburguer, J, Turetski, T, Kapeller, I & Deresiewicz, R. 1991. Highly repeated short DNA sequences in the genome of *Schistosoma mansoni* recognized by a species-specific probe. Molecular and Biochemical Parasitology 44: 73–80). The design of the primers was done after the visual inspection of the original sequence, so as to avoid the presence of complementary regions within each initiator or between both primers. In order to facilitate the amplification of the degraded DNA molecules (as expected for free DNA present in faeces or body fluids) the primers were chosen in a manner so as to amplify a short sequence. Also, all the stages of the present invention were strictly standardised in a manner as to function satisfactorily with chemically complex biological samples such as faeces and serum.

To the present moment, the use of PCR as a method for diagnosing human Schistosomiasis has never been related.

As such, it becomes evident that the search for a rapid and efficient method for the detection of the *Schistosoma* sp. parasite, specially useful in cases of low infection intensity, has not yet been viable. Thus, aiming to attain this objective, a strategy for PCR employing primers complementary to a specific and highly repetitive sequence of the *S. mansoni* genome, is used.

SUMMARY OF THE INVENTION

The object of the present invention is the detection of *Schistosoma* sp. in biological samples by PCR.

A first embodiment of the present invention refers to a method for the diagnosis of *Schistosoma* through the amplification by PCR of a DNA sequence of *Schistosoma* sp. The method of the present invention is characterised by the stages of:
 (a) collection of the sample to be tested;
 (b) extraction of the *Schistosoma* sp. DNA from the sample obtained in stage (a);
 (c) amplify a region of the *Schistosoma* DNA extracted in stage (b) with specific primers constructed from the original sequence described in SEQ ID NO:1;
 (d) separate the products of the amplifications of stage (c) by electrophoresis, followed by detection using appropriate colouring methods.

In a second embodiment, the invention is directed to a diagnostic kit to be used in the detection of *Schistosoma*. A basic kit includes all the reagents necessary for carrying out the PCR technique, namely: specific primers, nucleotides and appropriate buffer solution for the amplification by PCR. Optionally, the kit may contain the enzyme Taq polymerase in quantities sufficient for amplification, standard DNA to be used as positive control of the reaction, buffer solution of the sample to prepare the amplified material for electrophoresis and protocol and instructions manual for the user.

BRIEF DESCRIPTION OF THE DIAGRAMS

FIG. 1: Shows the DNA sequence (SEQ ID NO:1) of the repeater unit of *S. mansoni*. It indicates, in bold type, the localisation of the specific primers described in the present invention.

FIG. 2: Demonstrates the sensitivity of the PCR in the detection of the *S. mansoni* DNA.

Figure 3:
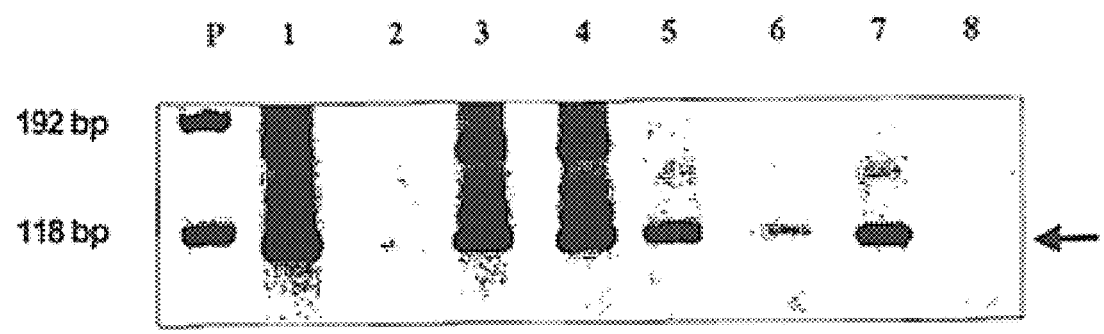

FIG. 3: Shows the capacity of the PCR technique of the present invention to amplify the DNA of various species of *Schistosoma* sp., including the three species of greater clinical-epidemiological importance in the world: *S. mansoni, S. japonicum* and *S. heamatobium*.

Figure 4:
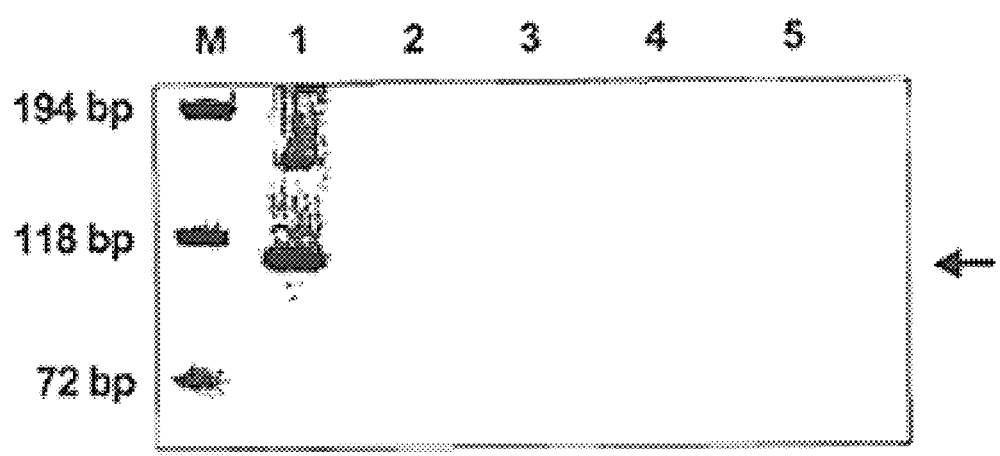

FIG. 4: Shows the specificity of the PCR of the present invention.

Figure 5:
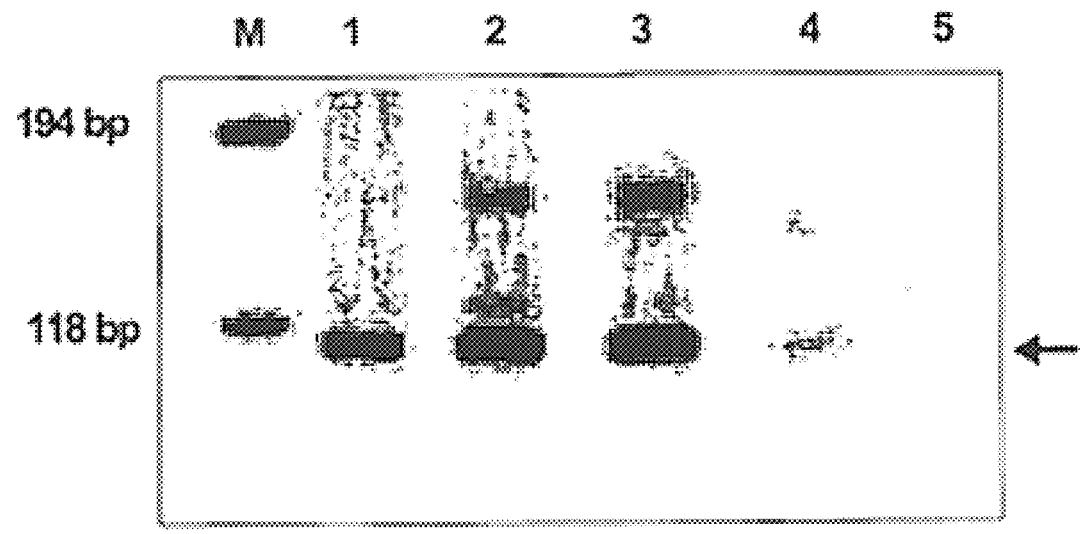

FIG. 5: Illustrates the comparison in terms of sensitivity between the PCR of the present invention and the parasitological test for the diagnosis of *S. mansoni* in human faeces.

Figure 6:
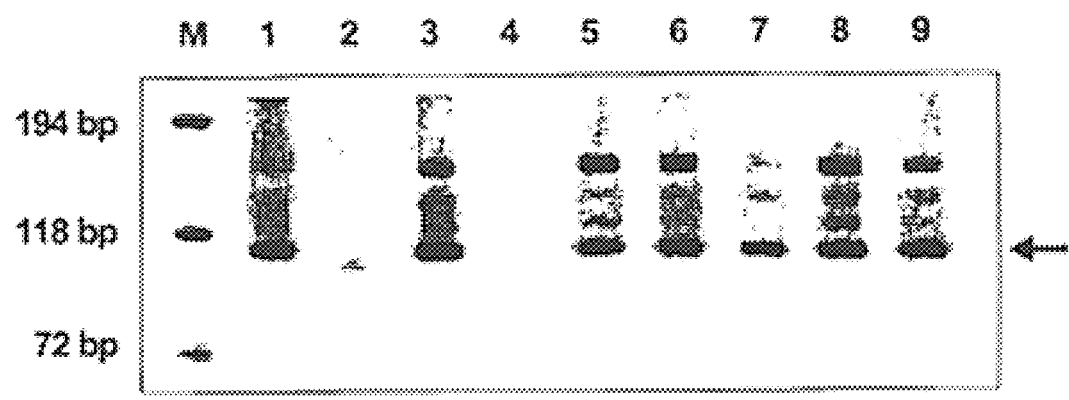

FIG. 6: Shows the detection, by PCR, of *S. mansoni* DNA in faecal samples of infected patients.

Figure 7:
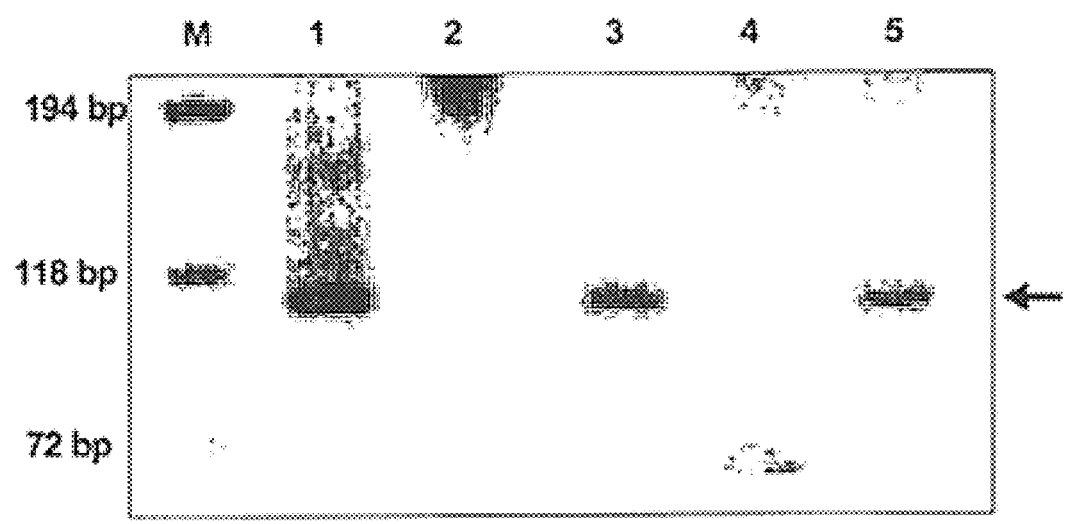

FIG. 7: Shows the detection, by PCR, of *S. mansoni* DNA in samples of human serum.

DETAILED DESCRIPTION OF THE INVENTION

So as to facilitate comprehension of the invention, the following are the readily accepted definitions of some terms used in this description:
1. Primers: single strand synthetic oligonucleotide, normally used in pairs in hybridisation with strands complementary to a DNA section. The inner extremities of the primer/DNA template complex are used by the DNA polymerase as points of initiation of the synthesis in a PCR.
2. Polymerase Chain Reaction (PCR): technique involving the application of cycles of denaturation, annealing with the primer and extension with a thermostable DNA polymerase, e.g. the Taq DNA polymerase, to amplify a target sequence of DNA. The PCR process for amplifying nucleic acid is described in the documents U.S. Pat. No. 4,683,195 and U.S. Pat. No. 4,683,202.

An inadequate choice of primers may produce various undesirable effects, such as: impossibility of amplification, amplification at various sites, formation of primer dimers, amongst others, rendering the amplification reaction non-informative.

The object of the present invention is accomplished by the amplification, by PCR, of a specific region of the *Schistosoma* sp. *genoma* and latter separation by electrophoresis of the products of this amplification, followed by appropriate colouring techniques that permit an adequate visualisation of the DNA in the gel including, but not limited to: colouring by silver salts, radioisotopes and enzymes combined with substrates that permit their detection, without the undesirable effects mentioned above.

The method of the present invention may be employed for the detection of the DNA of the genera *Schistosoma* in any biological sample that contains cells or DNA free of the parasite having sufficient integrity to be amplified by PCR. Some samples, such as faeces and urine, need to be submitted to some kind of treatment so that the membranes or envelopes that may eventually enclose the DNA in the cell of the parasite, may be ruptured, releasing the DNA in solution. Other samples, e.g. the serum of infected people, already contains the free molecules and do not need such treatment. Generally, the membranes can be ruptured by the use of special chemical substances, such as detergents and chaotropic salts, or by using physical and mechanical processes, such as induced osmotic pressure and sonication. After the rupture of the cell membranes, the DNA must be isolated from the other cell molecules, which can also be done by physicochemical processes, such as precipitation by ethanol or with the use of silica matrixes.

Once free in the solution, the DNA may be detected in the sample, after amplification by PCR. The DNA must be, preferentially, purified employing standard techniques for the removal of eventual substances that inhibit the amplification reaction.

After extraction, the DNA is selectively amplified by Polymerase Chain Reaction. Through the PC a specific sequence of the *Schistosoma* sp. *genoma* is selectively copied millions of times, permitting the detection of the parasite DNA. The reaction is a sequential process that requires at least two primers, small sequences of DNA complementary to the parasite DNA, that will be extended enzymatically, presenting a faithful copy of this DNA. Adding large quantities of primers, together with other necessary reagents, millions of copies of the parasite DNA are obtained. The primers of the PCR employed here were specially designed for this invention, based on the original highly repetitive sequence of the *S. mansoni genoma* as described in SEQ ID NO:1 and also illustrated in FIG. 1. It must be understood that other primers may be constructed having nucleotide sequences that are functionally equivalent in relation to SEQ ID NO:2 and SEQ ID NO:3. Such sequences are termed equivalent if functionally the corresponding biopolymers can perform the same role, without being identical, in view of the usage or purpose considered. The equivalent sequences may be the result of variability, as such, any modification in a sequence, spontaneous or induced, whether by substitution and/or deletion and/or insertion of nucleotide, and/or extension and/or shortening of the sequence at one of its extremities. An unnatural variability can result from genetic engineering techniques.

Each primer of the pair is, preferentially, constructed in a manner as to be substantially complementary to a different strand of the sequence that flanks the specific sequence of the *Schistosoma* sp. *genoma* to be amplified. Thus, a primer from each pair is sufficiently complementary to be able to hybridise with a part of the sequence in the sense and the other primer of each pair is also sufficiently complementary to hybridise with a different part of the same sequence in the antisense. Despite the sequence of the primer not necessarily needing to mirror the exact sequence of the template, the closer the terminal 3' sequence corresponds to the exact sequence the better the link during the matching stage of the polymerase chain reaction.

The primers may be prepared by any appropriate method known to those skilled in the art and include, for example, cloning and digestion of adequate sequences and direct chemical synthesis.

The product from the amplification promoted by PCR is a fragment, or a series of DNA fragments of different sizes which can be separated through electrophoresis, followed by appropriate techniques of colouring which allow adequate visualisation of the DNA in gel. Due to the great specificity of PCR, the amplified DNA of the parasite can be differentiated from the other products of the amplification based on its specific size. In this manner, the presence or absence of the infection can be determined, most times, simply by visual analysis of the amplified products, therefore, by the presence or not of the fragment with a weight corresponding to that of the parasite. In the present invention, the is employed to amplify and visualise a specific fragment of DNA originally described in *S. mansoni*, and also amplify specific regions of other species of *Schistosoma*, leading to the conclusion that the repetitive and specific region of the DNA originally verified in *S. mansoni* and described in SEQ ID NO:1 is common to all the other species of *Schistosoma*.

The amplification of the specific region of the *Schistosoma* sp. *genoma* is done by PCR, with the primers specially constructed to be used in the present invention and defined in Table 1 or functionally equivalent sequences, therefore, that are capable of amplifying the sequence of *S. mansoni* or homologous sequences of other species of *Schistosoma*.

TABLE 1

Primers employed in the reaction by PCR for the amplification of the highly repetitive region of the Schistosoma sp. genoma.

| SEQ ID NO: | Primers |
|---|---|
| 2 | 5'-GATCTGAATCCGACCAACCG-3' |
| 3 | 5'-ATATTAACGCCCACGCTCTC-3' |

The kit of the present invention includes all the reagents necessary to allow the detection of any infection caused by helminths of the genera *Schistosoma*. The kit consists of specific primers for a specific region of the *Schistosoma* sp. *genoma* as shown in Table 1 or functionally equivalent sequences and, furthermore, reagents and additives normally used in the PCR technique are also supplied, e.g. appropriate nucleotide, such as dGTP (desoxyguanidine-triphosphate), dATP (desoxyadenosine-triphosphate), dCTP (desoxycitidine-triphosphate) and dTTP (desoxytimidine-trisphosphate); appropriate buffer solution (e.g. 10 to 20 mM of Tris-HCl, 50 to 60 mM of KCl, 1.5 to 2.0 mM of $MgCl_2$, pH 8.0 to 8.5); Taq DNA polymerase, preferentially. A certain quantity of DNA to be used as a positive control of the reaction will also be supplied, along with an instructions manual containing the protocol to be used in the test, with an illustrative diagram of the results to be expected.

The present invention is described in detail through reference to the following examples. It must be understood that the present invention is not limited to these examples but also includes variations and modifications within the scope of the functions of the invention.

EXAMPLE 1

Rupture of the Eggs of S. mansoni

The eggs of S. mansoni were extracted from the livers of mice previously infected with 100 cercariae, and stored in 0.9% saline solution at −20° C. until being used (Pellegrino e Siqueira, 1956, Rev. Bras. Malar. 8: 589). For the rupture of the eggs, 10 μl of the saline solution containing 100.000 eggs/ml was mixed with 90 μl of distilled water and the final solution submitted to 5 minutes of agitation in a mechanical mixer. This mixture, containing ruptured eggs, was used directly in the extraction of the DNA.

EXAMPLE 2

Extraction of DNA, through a Modification of the Steiner Method (Steiner, J. J., C. J. Poklemba, R. G. Fjellstrom and L. F. Elliott. 1995. A rapid one-tube genomic DNA extraction process for PCR and RAPD analyses. Nucleic Acids res. 23 (13): 2569–2570).

100 μl of the ruptured egg solution was diluted in 200 μl of buffer containing 10 mM of Tris-base, pH 8.0; 270 mM of EDTA, pH 8.0; 1% of Sodium Dodecyl Sulphate (SDS); 1% of polyvinylpolypyrrolidone (PVPP). This mixture was incubated at 95° C. for 20 minutes, with a rapid manual agitation after the first 10 minutes of incubation and, then centrifuged for 10 minutes at 8000×g, at room temperature. The DNA contained in the skim was precipitated with ethanol, the skim was removed and the precipitate was incubated for 15 minutes at 37° C. for the evaporation of the remaining alcohol and later replaced in suspension in buffer T.E. (10 mM of Tris, pH 8.0; 1 mM of EDTA, pH 8.0). The DNA was then quantified by optical density reading at 260 nm, and stored at −20° C. until being used in the PCR.

EXAMPLE 3

Amplification by Polymerase Chain Reaction Employing the Specific Primers Shown in Table 1:

Briefly, 1 μl of extracted DNA was submitted to amplification in a reaction tube containing PCR buffer (20 mM Tris-HCl pH 8.0, 50 mM de KCl, 1.5 mM $MgCl_2$), 200 μM dNTPs (deoxinucleotides), 0.5 μM of each primer and 0.75 Units of Taq Polimerase enzyme, in a total volume of 10 μl. The amplification reaction involved denaturation of the double-stranded parasite DNA at 95° C.; for 45 seconds and primer annealing at 63° C.; for 30 seconds. These two steps were repeated sequentially in 35 consecutives cycles. In the first cycle, the denaturation step was prolonged for five minutes, in order to assure complete denaturation, and at the last cycle an additional step, at 72° C.; for 2 minutes, was included to finalise the extension of the remaining annealed primers.

FIG. 2 shows the electrophoretic pattern obtained from the amplification of the DNA of S. mansoni and, also, the maximum sensitivity obtained for the detection of this DNA. In lane M is the molecular weight marker; in lanes 1 to 5: 20, 10, 5, 1 and 0.5 fg of DNA, respectively. The reaction by PCR was capable of detecting down to 1 fg of S. mansoni DNA. FIG. 3 shows the electrophoretic pattern obtained after the amplification of the DNA of five other species of genus Schistosoma, amplified with the same primers and in the same PCR conditions as used for S. mansoni. Lane M: molecular weight marker; lane 1: DNA of S. mansoni; lane 2: S. haematobium; lane 3: S. japonicum (strain from the Phillipines); lane 4: S. japonicum (strain from Japan); lane 5: S. matthei; lane 6: S. bovis; lane 7: S. leipperi; lane 8: negative control. The PCR reaction was capable of amplifying the DNA of all the species of Schistosoma sp. tested. FIG. 4 shows the attempt to amplify the DNA of worms of other genera, also under the same conditions used for S. mansoni. Lane M: molecular weight m arker; lane 1: positive control (DNA of S. mansoni); lane 2: Ascaris lumbricoides; lane 3: Ancilostoma duodenales; lane 4: Taenia solium; lane 5: Trichiuris trichiuria. No product of amplification can be visualised when using the DNA of worms of other genera. The PCR described in this invention is, therefore, specific for genera Schistosoma.

EXAMPLE 4

Detection of the S. mansoni DNA in Faecal Samples of Patients:

In these experiments, the eggs co ntained in the infected faeces (naturally or artificially) were ruptured in the manner described in Example 1. The DNA was then extracted from the faeces by the same technique used for the extraction of DNA from pure S. mansoni eggs (Example 2).

After extraction, 1 μl of the S. mansoni (diluted 100 times) was amplified with the same primers and in the same conditions described in Example 3. FIG. 5 shows the products of the amplification of the S. mansoni DNA in faeces artificially infected with the eggs of the parasite. Briefly, 100 mg of a faecal sample of a patient, containing 216 eggs/gramme, was mixed to 900 mg of negative faeces, forming a sample with an expected concentration of approximately 20 eggs/gramme. This procedure was repeated two more times originating faeces samples with 2 and 0,20 eggs/gramme, approximately. An aliquot of each sample was then submitted for analysis by the Kato-Katz method an for detection of the parasite DNA by the PCR of the invention, with the aim of comparing the sensitivity of the two methods. In lane M is the molecular weight marker; lane 1: positive control (0.1 ng of S. mansoni egg DNA); lanes 2 to 5: amplified DNA of samples containing 200, 48, 4.8 and 0.48 eggs/gramme of faeces, respectively. The PCR was capable of detecting the DNA of S. mansoni down to the sample containing approximately 4.8 eggs/gramme, whilst the sensitivity of the Kato-Katz method was of 48 eggs/gramme, therefore, 10 times lower.

FIG. 6 shows the result of the amplification of the S. mansoni DNA in faeces of patients with various concentrations of parasites, previously determined by the Kato-Katz method. Lane M: molecular weight marker; lane 1: positive control; lanes 2 to 9: samples of human faeces containing 0.96; 0.168; 432; 600; 96.912 and 72 eggs/gramme, respectively. The result of the PCR was in accordance with those obtained by the parasitological test in all the samples.

EXAMPLE 5

Detection of S. mansoni in the serum of patients.

The DNA of 4 samples of serum was purified using 100 μl/sample employing the GLASS-MAX® DNA isolation spin cartridge system (Lite Technologies), in accordance with the instructions of the manufacturer. 2 μof this DNA were then used in the amplification by PCR, in the same conditions described above. The serum from persons previously examined by the Kato-Katz method was used, having 2 positive and 2 negative samples.

FIG. 7 shows the result of this amplification. In lane M is the molecular weight marker; lane 1: positive control; lanes 2 to 5: serum of persons containing 0; 96; 0 and 216 eggs/gramme of faeces respectively.

What is claimed is:

1. A method for the detection of parasites of the *Schistosoma* genus in a biological sample, said method comprising the steps of:

(a) extracting *Schistosoma* sp. DNA from a biological sample;

(b) amplifying by PCR a specific region of said *Schistosoma* sp. DNA obtained in step (a) with a primer pair consisting of SEQ ID NO:2 and SEQ ID NO:3, to obtain amplified products; and, (c) separating the amplified products obtained in step (b) by electrophoresis to obtain separated products, and visualizing said separated products to detect the presence of any parasites of the *Schistosoma* genus in the biological sample.

2. The method according to claim 1, wherein in step (c) the amplified products of step (b) are separated by electrophoresis in polyacrylamide gel and visualized by colouring with silver salts.

3. A primer pair consisting of SEQ ID NO:2 and SEQ ID NO:3.

4. A kit to detect the presence of an organism of the genus *Schistosoma* in a biological sample, said kit comprising a primer pair consisting of SEQ ID NO:2 and SEQ ID NO:3.

5. The kit according to claim 4, further including a protocol and instruction manual.

* * * * *